United States Patent [19]

Birum

[11] Patent Number: 5,373,583

[45] Date of Patent: Dec. 20, 1994

[54] TORSIONALLY BIASED POSITIONABLE MOUNT

[76] Inventor: Donald A. Birum, Rte. 1 Box 163, #2 Oriole Dr., Agency, Mo. 64401

[21] Appl. No.: 975,204

[22] Filed: Nov. 12, 1992

Related U.S. Application Data

[63] Continuation of Ser. No. 658,998, Feb. 21, 1991, abandoned, which is a continuation-in-part of Ser. No. 459,467, Jan. 2, 1990, Pat. No. 5,052,054.

[51] Int. Cl.$^5$ .................................................. A42B 1/24
[52] U.S. Cl. .......................................... 2/10; 2/209.13; 2/422; 403/61
[58] Field of Search .............. 2/10, 13, 185 B, 185 C, 2/185 R, 196, 199, 209.1, 209.2, 422, 6.3, 6.3, 6.5, 6.7, 15, 209.13; 24/666; 403/53, 59, 61

[56] References Cited

U.S. PATENT DOCUMENTS

| | | | |
|---|---|---|---|
| 857,838 | 6/1907 | Shaw | 2/453 |
| 860,322 | 7/1907 | Paroubek | 2/10 |
| 1,091,332 | 3/1914 | Hart | 403/61 |
| 2,725,560 | 12/1948 | Feldman | 2/10 |
| 2,772,901 | 12/1956 | Roethel | 403/61 |
| 3,038,377 | 6/1962 | Maxson | 88/52 |
| 3,273,164 | 9/1966 | Thomas | 2/10 |
| 3,373,444 | 3/1968 | Militello | 2/10 |
| 3,709,585 | 1/1973 | Tsai | 403/61 |
| 4,109,320 | 8/1978 | Anderson | 2/10 |
| 4,397,047 | 8/1983 | Nava | 2/10 |
| 4,577,347 | 3/1986 | Connon | 2/422 |
| 4,734,940 | 4/1988 | Galet | 2/422 |
| 4,869,586 | 9/1989 | Chung | 2/10 |
| 4,918,753 | 4/1990 | Mermillod | 2/10 |
| 4,958,264 | 9/1990 | Evendon | 2/422 |
| 5,052,054 | 10/1991 | Birum | 2/185 R |

FOREIGN PATENT DOCUMENTS

| | | | |
|---|---|---|---|
| 995665 | 6/1965 | United Kingdom | 2/10 |
| 1405099 | 7/1975 | United Kingdom | 2/10 |
| 1549399 | 8/1979 | United Kingdom | 2/10 |
| 2015868 | 9/1979 | United Kingdom | 2/10 |

Primary Examiner—Clifford D. Crowder
Assistant Examiner—Diana L. Biefeld

[57] ABSTRACT

A positionable mount is demonstrated as a headgear implement-mount (28) supporting an eyewear front (30) through a resilient appendage (68). The implement-mount includes a friction surface (50) cooperating with a headed stud (52) to establish a constraint-dimension (62). The appendage is formed with an edged-channel cross section and includes an elongated slot (76) for receiving the implement-mount headed stud. In engaging the implement-mount, the appendage cross section is torsionally, deformably constricted in a manner creating resiliently biased friction between the appendage edges (72) and the friction surface, thereby holding the eyewear implement in a selected position relative to the headgear. Because the appendage with implement-mount engagement is resiliently biased, the implement position may be hand adjusted. The appendage with implement-mount engagement may be influenced by a pair of hand operators (100). As the operators are worked in a pinching movement, the appendage cross section is dimensionally reduced to less than the implement-mount constraint-dimension, thereby freeing the appendage and the attached implement to be conveniently repositioned relative to the headgear.

31 Claims, 1 Drawing Sheet

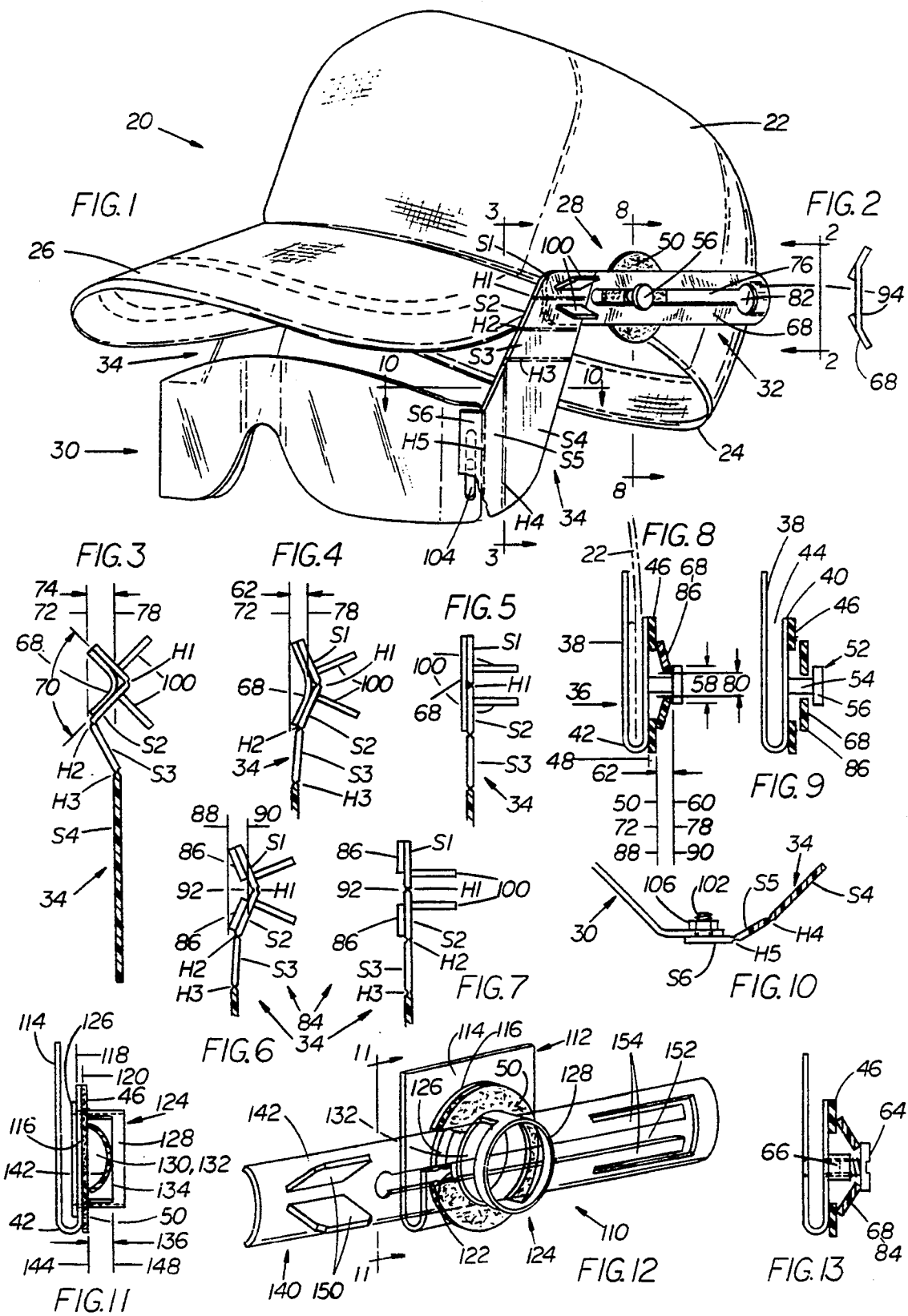

TORSIONALLY BIASED POSITIONABLE MOUNT

This is a continuation of application Ser. No. 07/658,998, filed Feb. 21, 1991, now abandoned, which is a continuation-in-part of application Ser. No. 07/459,467, filed Jan. 2, 1990, now U.S. Pat. No. 5,052,054.

BACKGROUND-FIELD OF INVENTION

This invention relates to mounts for headgear supported implements, especially to a positionable mount for sight-cooperative implements such as eyewear.

BACKGROUND-DESCRIPTION OF THE PRIOR ART

Sight related devices are commonly used with or supported from a headgear. For example, protective eyewear or face shields are often used in conjunction with a hardhat or other headgear. Similarly, safety or sunglasses are often used at work and outdoors while wearing a soft utility style billed cap, and inventors have provided devices for mounting eyewear directly from billed caps.

Since the frontal bill is normally the only structured portion of a soft cap, the predominate prior art relating to eyewear mounted from soft caps is directed towards arrangements in which the eyewear is supported from the cap bill. This course is exemplified by U.S. Pat. No. 2,725,560 to Feldman (1948), which demonstrates a cap bill modified with underside channeled tracks to engage swivels joined to an eyewear.

A less prevalent approach for mounting eyewear from a headwear is demonstrated by devices in which modified temple elements link the eyewear front with the headwear crown. U.S. Pat. No. 857,838 to Shaw (1907), discloses an eyewear modified with links jointed to the temple bars. Each link end is freely pivoted to the headwear crown by a fastener passing through the link and the crown material.

While these devices relate utility as mounts for headgear supported eyewear, they also demonstrate disadvantages associated with prior art in the field of positionable mounts for headgear supported sight-cooperative implements:

(a) The device does not provide a headgear-eyewear mount in which the eyewear is vertically positionable relative to the eyes of the wearer (Feldman).

(b) The device does not offer a headgear-eyewear mount wherein the attitude at which the headgear may be worn is independently selectable relative to the eyewear position (Feldman).

(c) The headgear-eyewear mount requires that the eyewear rest on the nose of the wearer (Shaw).

(d) The devices do not provide a headgear-eyewear mount wherein an eyewear is concurrently disengagable from the mount and repositionable relative to the headgear by use of a common operator.

OBJECTS AND ADVANTAGES

Accordingly, several objects and advantages of the invention are:

(a) to provide a mount for a headgear supported sight-cooperative implement, and especially eyewear implements, wherein the eyewear is vertically positionally adjustable relative to the eyes of a wearer;

(b) to offer a headgear implement mount wherein the attitude at which the headgear may be worn is independently selectable relative to the implement position;

(c) to provide a mount for a headgear supported eyewear wherein the eyewear does not necessarily rest on the nose of the wearer;

(d) to provide a headgear-eyewear mount wherein the eyewear is disengagable from the mount and repositionable relative to the headgear by use of a common operator.

A further object of the invention is to provide a positionable mount for a headgear implement which does not necessarily require a threaded member for attaching the implement to the headgear or securing the position of the implement relative to the headgear. Still further objects and advantages of the invention will become apparent from a consideration of the drawings and ensuing description.

DRAWING FIGURES

In the accompanying drawings like reference numerals are used to indicate like parts in the various views.

FIG. 1 is a perspective view, partially broken away, showing a headgear (cap) with a mounted implement (eyewear), the eyewear to cap mount demonstrating a preferred embodiment of the invention.

FIG. 2 is an isolated view, taken from perspective 2—2 of FIG. 1, showing an eyewear temple appendage end portion in profile.

FIG. 3 is a partial sectional view taken along line 3—3 of FIG. 1, showing an eyewear temple appendage in unconstrained profile.

FIG. 4 is a partial sectional view taken along line 3—3 of FIG. 1, partially broken away, showing the eyewear temple appendage of FIG. 3 in constrained profile, in correspondence with FIG. 8.

FIG. 5 is a partial sectional view taken along line 3—3 of FIG. 1, partially broken away, showing the eyewear temple appendage of FIG. 3 in released profile, in correspondence with FIG. 9.

FIG. 6 is a partial sectional view taken along line 3—3 of FIG. 1, partially broken away, showing an alternate embodiment of the invention wherein an eyewear temple appendage has paired members, the paired members being in constrained profile in correspondence with FIG. 8.

FIG. 7 is a partial sectional view taken along line 3—3 of FIG. 1, partially broken away, showing the eyewear temple appendage of FIG. 6 in released profile in correspondence with FIG. 9.

FIG. 8 is a sectional view taken along line 8—8 of FIG. 1, in correspondence with FIGS. 4 and 6, showing an implement-mount in profile and an eyewear temple appendage in constrained sectional relation to the implement-mount.

FIG. 9 is a sectional view taken along line 8—8 of FIG. 1, in correspondence with FIGS. 5 and 7, showing an implement-mount in profile and an eyewear temple appendage in released sectional relation to the implement-mount.

FIG. 10 is a partial sectional view taken along line 10—10 of FIG. 1, showing an eyewear front connection with a transition member.

FIG. 11 is a sectional view taken along line 11—11 of FIG. 12.

FIG. 12 is a perspective view of an alternate embodiment of the invention wherein an implement-mount includes a rotatable member.

FIG. 13 is a sectional view taken along line 8—8 of FIG. 1, showing an implement-mount in profile and an eyewear temple appendage in sectional relation to the implement-mount, the implement-mount having a variable constraint-dimension.

DESCRIPTION AND OPERATION

Referring to the drawings in more detail and initially to FIG. 1, numeral 20 generally designates a headwear as a baseball style or utility type soft cap. The cap has a hollow crown body 22 which is sized and shaped to fit the head. The crown is typically constructed from a lightweight flexible fabric which forms a pliant crown rim 24. A relatively stiff frontal bill 26 is joined to the crown rim.

In accordance with the invention (FIG. 1), cap 20 is provided with an implement-mount (s) 28. The implement-mount may be installed along the cap crown temple region. A pair of implement-mounts positioned at opposing crown temple regions would be preferred to mount an eyewear 30 as demonstrated in FIG. 1 (the far side mount is not visible). Each implement-mount provides a supportive interface to the eyewear front by engaging a modified temple appendage 32 (the far side appendage is not visible). Each temple appendage is joined to the eyewear front through a transition 34 (the far side transition is partially visible).

Implement-mount 28, shown in perspective in FIG. 1 and in profile in FIGS. 8, 9 and 13, may be embodied as a detachable clip 36 (referenced collectively between FIGS. 8 and 9). Clip 36 may be produced from a lightweight durable material such as plastic. Clip 36 includes an interior plate 38 which joins an exterior plate 40 through a U-shaped bight section 42. Spacing of the clip plates forms a clip throat 44 which is sized to engage the cap crown body 22 by slipping over the crown rim 24.

A friction enhancing member, depicted by a rubber washer 46, shown in section in FIGS. 8, 9 and 13, may be joined to the outside face 48 of the exterior clip plate 40. Washer 46 presents a friction surface 50 (FIGS. 1 and 8).

A circumferentially accessible headed stud 52, referenced collectively between FIGS. 1, 8 and 9, may also be joined to the outside face of the exterior clip plate 40. Stud 52 includes a stem 54 (FIG. 9) and a head 56 having a head diameter 58. Stem 54 spaces the underside surface 60 of head 56 apart from the friction surface 50, thus establishing a constraint-dimension or opening 62 (FIG. 8). In a modified arrangement illustrated in FIG. 13, the constraint-dimension may be dimensionally varied by threading a headed screw 64 into or out of a mating stud 66 which is joined to the outside face of the exterior clip plate.

As shown in FIGS. 1-4, the eyewear temple appendage 32 may be embodied as a semirigid arm 68 having a channeled profile. Arm 68 may be produced from a lightweight durable material exhibiting the property of elastic memory, for example polycarbonate plastic. Arm 68 may be formed with an angled cross section 70 similar to a flattened-V (FIG. 3). The arm cross section exposes two arm edges 72. The arm cross section 70 has an unconstrained width 74 dimensionally greater than the implement-mount constraint-dimension or opening 62 (FIG. 8). Arm 68 may include an elongated slot 76 (FIG. 1) bounded by slot edges 78. Slot 76 has a width 80 less than the stud head diameter 58 (FIG. 8). Slot 76 may be provided with an opening 82 (FIG. 1) dimensionally greater than the stud head diameter, thus permitting stud 52 convenient access to or egress from the slot.

In operation, FIGS. 1, 4 and 8, arm 68 engages implement-mount 28 as the headed stud 52 is received by the temple appendage arm elongated slot 76. In engaging the implement-mount, the resilient cross section of arm 68 is constricted by the cooperative constraint members, friction surface 50 and stud head 56. The constricted engagement (FIG. 8) causes arm edges 72 to resiliently bear on friction surface 50 as slot edges 78 bear on the underside surface 60 of stud head 56. The resilient engagement of the temple appendage arm with the implement-mount is sufficient to frictionally hold the eyewear implement in a selected position relative to the headgear. Because the edge-on-surface clutching contact between arm edges 72 and friction surface 50 is resiliently biased, the implement position may be hand adjusted.

As shown in FIGS. 6 and 7 in profile, the temple appendage 32 may be embodied as a semirigid arm 84 having paired legs 86. Each leg 86 has an outside edge 88 and an inside edge 90. Arm 84 is comparable to arm 68 in features, except the elongated slot 76 of arm 68 is extended at the forward end to form an open slot 92 (shown in profile in FIGS. 6 and 7). Slot 92 is bounded by legs 86. In correspondence with arm 68, arm 84 also forms an unconstrained cross section 70 (not shown but dimensionally like that of arm 68, FIG. 3) having a width 74 dimensionally greater than constraint-dimension or opening 62. Since slot 92 is open at the forward end, the arm cross section is generated from the formed end portion 94, shown in profile in FIG. 2. Slot 92 is closed off by the adjoining transition member 34 (FIGS. 6 and 7).

In operation, FIGS. 6 and 8, arm 84 engages implement-mount 28 as the headed stud 52 is received by slot 92. In order to engage the implement-mount constraint members, each leg 86 resiliently, axially twists in an opposite direction, thus dimensionally reducing the cross section width of arm 84. The resilient, axial twisting causes each leg 86 outside edge 88 (FIG. 8) to torsionally bear on friction surface 50 as each leg inside edge 90 torsionally bears on the underside surface 60 of stud head 56. Friction surface 50 and stud head 56 function cooperatively as a torsion-constraint in engaging each leg 86. The torsional engagement of the temple appendage arm 84 with the implement-mount is sufficient to frictionally hold the eyewear implement in a selected position relative to the headgear. Because the edge-on-surface contact between leg edges 88 and friction surface 50 is resiliently biased, the implement position may be hand adjusted.

The transition 34, FIGS. 1-7 and 10, connects the eyewear front 30 to the forward end of each temple appendage arm 68 or arm 84. The transition upwardly offsets the temple appendage from the eyewear front while maintaining a normal orientation between the longitudinal axis of the temple appendage and the general plane of the eyewear front. The offset enhances positionability of the eyewear front and increases clearance between the temple appendages and the ears of a wearer.

Transition 34, FIG. 1, may be produced from a thin durable material such as plastic. The plastic, such as polyethylene or polypropylene, may exhibit the property of forming a living-hinge when the material is creased or provided with a delineation offering decreased resistance to folding. The living-hinge is incorporated with transition 34 as multiple plastic hinges H1, H2, H3, H4 and H5. The hinges define the boundaries between transition segments S1, S2, S3, S4, S5 and S6.

Hinge H1 is generally aligned with the central longitudinal axis of the temple appendage arm 68 or arm 84. Hinge H1 separates transition segments S1 and S2. The transition segments S1 and S2 are joined with arm 68. (FIG. 3) or arm 84 (FIG. 5) in a back to face relation. Each transition segment S1 and S2 may be provided with a projecting operator 100. The operators are sized and located to cooperate with the human hand and function to influence the temple appendage to implement-mount engagement by deforming the cross section of arm 68 or arm 84.

In operation, FIGS. 5 and 7, operators 100 work by finger force. A pinching movement causes transition segments S1 and S2 to hinge from hinge H1. The cross section of the attached temple appendage arm 68 or 84 is dimensionally reduced (FIG. 9) to less than constraint-dimension or opening 62 (FIG. 8). Reducing the arm cross section frees arm 68 or arm 84 from engagement with the implement-mount constraint members. The arms are then free to translate or pivot relative to implement-mount 28, and the attached implement (eyewear front 30) may be repositioned relative to the headgear (cap 20).

The eyewear front 30 may be adjusted in towards or out away from the cap and the eyes of the wearer, by pinching the operators 100 and repositioning the implement in or out as permitted by the elongated shape of slot 76 (arm 68) or slot 92 (arm 84). In addition, with the arms disengaged, the eyewear front 3 0 may be concurrently pivoted upwardly or downwardly about the horizontal axis of the opposite side implement-mount headed studs 52. The eyewear front is thus provided with combined-concurrent-multidirectional or up-down-concurrent-in-out, wearer selectable positioning. When the operators are released, the arms 68 or 84 resiliently re-engage the implement-mount constraint members as previously described.

Hinges H2 and H3, FIG. 1, may be in general alignment with hinge H1 and bound transition segment S3. Segment S3, shown in FIGS. 3-7 in profile, is free to hinge in alternate directions, thereby adapting to dimensional variations between the temple appendages required by differing cap and head sizes. Concurrently, each temple appendage can axially turn from hinge H2 and secondarily turn from hinge H3, thus bringing the common plane of the temple appendage arm edges 72 (FIG. 4) or leg edges 88 (FIG. 6) into alignment with the plane of the implement-mount friction surface 50 (FIG. 8).

Hinges H4 and H5, FIG. 1, may be oblique to hinges H1, H2 and H3 and bound transition segment S5. As shown in FIG. 10 in partial section, segments S4 and S5 are free to hinge in alternate directions, thus allowing the eyewear temple appendages to remain parallel with the plane of each opposite side friction surface 50 while adjusting to variations in dimensional separation as described.

End transition segment S6, FIGS. 1 and 10, is bounded by hinge H5. Segment S5 may include an integral projecting threaded stud 102 (FIG. 10) or other fastener for joining the eyewear front 30 with the end transition segment. As shown in FIG. 1, the threaded stud 102 may be received by a vertical elongated slot 104 located at each peripheral end of the eyewear front (the far side slot is not visible). A mating nut 106 (FIG. 10) is threaded onto stud 102 to secure the eyewear front to the transition. The eyewear front may be adjusted vertically, relative to transition 34, within the range permitted by the length of slot 104. Limited pivotal adjustment of the eyewear front relative to the transition is also possible. When adjustments are completed, nut 106 is tightened on stud 102 to secure the selected orientation.

An alternate arrangement of the invention is illustrated and referenced collectively between FIGS. 11 and 12. An implement-mount 110 is embodied as a detachable clip 112 for joining with a supporting member (not shown). Clip 112 includes an interior plate 114 joined to an exterior plate 116 through U-shaped bight section 42. Exterior plate 116 has an interior surface 118, an exterior surface 120 and a circular opening 122. Opening 122 is sized to receive a rotatable member 124. The rotatable member includes a flanged base 126 joined with a cylindrical neck 128. Neck 128 has a diameter less than opening 122 and is free to turn within the clip plate opening as the flanged base 126 bears on the interior surface 118 of the exterior clip plate 116.

The rotatable member cylindrical neck 128 has a crosswise opening 130 defined by matching open segments 132 on opposite sides of the neck body (FIG. 11). The crosswise opening has a rectangular profile presenting constraint edges 134. The rubber washer 46 may be joined to the exterior surface 120 of the exterior clip plate 116 to provide the friction surface 50. The friction surface cooperates with constraint edges 134 to establish a constraint-dimension 136.

An implement appendage 140, demonstrated collectively between FIGS. 11 and 12, and shown unattached, includes a linear arm 142 having arm edges 144 and an elastic convex cross section with an apex 148. The unconstrained cross sectional width of arm 142 is dimensionally greater than constraint-dimension 136. Arm 142 is sized to enter the rotatable member crosswise opening 130.

In operation, arm 142 engages implement-mount 110 as arm 142 is received by crosswise opening 130. In engaging the implement-mount, the resilient cross section of arm 142 is constricted by the cooperative constraint members, friction surface 50 and rotatable member constraint edges 134. The constricted engagement causes are edges 144 to resiliently bear on friction surface 50 as arm apex 148 bears on the rotatable member constraint edges 134. The resilient engagement of the implement arm with the implement-mount is sufficient to frictionally hold the implement in a selected position relative to the supporting member. Because the edge-on-surface contract between arm edges 144 and friction surface 50 is resiliently biased, the implement position may be hand adjusted.

Arm 142 may include operations 150 (FIG. 12) which function to influence the constricted engagement. As operators 150 are manually worked in a pinching movement, the cross section of arm 142 is dimensionally reduced to less than constraint-dimension 136 (FIG. 11), thus allowing arm 142 to freely translate through crosswise opening 130. Additionally, when the arm cross section is reduced by utilizing operators 150, the rotatable member 124 is free to rotate, and arm 142 maybe pivoted about the axis of the rotatable member.

Arm 142, FIG. 12, may include a slit 152 along the central longitudinal axis of the arm. As operators 150 are worked, slit 152 functions to distribute operator influence along the length of the arm by weakening the cross sectional integrity of the arm. A pair of integral arm-fingers 154, adjacent and parallel to slit 152, also react to operator influence by reducing the arm cross section along the arm-fingers portion of the arm body. The arm-fingers, having been released from the surrounding arm material, will be disproportionately influenced when the operators are worked as previously described.

CONCLUSION, RAMIFICATIONS AND SCOPE OF INVENTION

From the foregoing, it will be seen that the invention provides a unique, highly functional positionable mount for a headgear supported implement, and especially an eyewear implement. Furthermore, the invention has additional advantages in that

- it provides a mount for a headgear supported implement, and especially eyewear implements, wherein the eyewear is vertically positionally adjustable relative to the eyes of a wearer;
- it offers a headwear implement mount wherein the attitude at which the headwear may be worn is independently selectable relative to the implement position;
- it provides a mount for headgear supported eyewear, wherein the eyewear does not necessarily rest on the nose of the wearer;
- it provides a headgear-eyewear mount wherein the eyewear is concurrently disengagable from the mount and repositionable relative to the headgear through a common operator;
- it provides a positionable mount for a headgear implement which does not necessarily require a threaded member for attaching the implement to the headgear or securing the position of the implement relative to the headgear.

While the above description contains many specificities, these should not be construed as limitations on the scope of the invention, but rather as an exemplification of several embodiments thereof. Other variations are possible. For example:

- a specific type of headgear is not required for cooperation with the invention, and the invention may be utilized with a variety of headgear including, but not limited to, caps, hats, visors, headbands, helmets, hardhats, headwear and headgear in general;
- a specific arrangement for joining the implement-mount with the headgear is not required, and the joining arrangement may utilize methods other than those described, including, but not limited to, an integral connection, stiching, hook and loop, adhesives, mechanical fasteners and fasteners in general;
- a specific implement is not required for cooperation with the invention, and the invention may be utilized with a variety of positionable implements including, but not limited to, sight-cooperative implements, light emitting sources, audio related components and other implements cooperating with the human senses in general;
- the underlying concept of a positionable mount, as disclosed in the preceding description, might be utilized in a form and on a scale unrelated to mounts for headgear implements, including, but not limited to, a positionable mount for a reading lamp or automobile sun visor.

It will be understood that certain features and subcombinations of the invention are of utility and may be employed without reference to other features and subcombinations.

Accordingly, the scope of the invention should be determined not by the embodiments illustrated, but by the appended claims and their legal equivalents.

I claim:

1. An assembly for use in attaching an implement to an associate unit comprising:
   - a first component including at least one elongate, resilient member having a substantially linear longitudinal axis and an exposed edge generally parallel to said axis;
   - a second component for engaging said first component, said second component including a generally planar surface and means for twisting said resilient member around said axis so as to effect torsionally biased frictional holding of said edge on said surface, whereby said implement may be held in a predetermined position relative to said associate unit.

2. The assembly of claim 1, wherein said first component includes resilient members for engaging said second component in torsional opposition.

3. The assembly of claim 2, wherein said resilient members are at least partially joined together through a flexible component.

4. The assembly of claim 1, wherein said resilient member comprises two substantially parallel longitudinal legs, each leg cooperating with the other to form an elastic channel-like cross section having at least two substantially aligned exposed edges for engaging said surface.

5. The assembly of claim 4, wherein said legs are at least partially joined together through a hingable component and disposed in torsional opposition.

6. The assembly of claim 1, wherein said components comprise means for providing combined multidirectional positioning of said first component relative to said second component, whereby said implement may be provided like positioning relative to said associate unit.

7. The assembly of claim 1, wherein said components comprise means for circumferentially engaging one with the other.

8. The assembly of claim 1, wherein said first component comprises means for varying the cross sectional integrity of at least a portion of said resilient member along the length thereof.

9. The assembly of claim 1, further including means for manually releasing the holding of said edge on said surface while said first and second components are engaged one with the other, whereby said implement may be conveniently positioned relative to said associate unit.

10. The assembly of claim 9, wherein said releasing means comprises means for resiliently deforming at least a portion of said first component.

11. The assembly of claim 9, wherein said first component includes members arranged in torsional opposition and said releasing means comprises means for distorting said members.

12. The assembly of claim 9, wherein said first component includes an elastic channel-like cross section, and said releasing means comprises means for altering said cross section.

13. The assembly of claim 9, wherein said releasing means additionally provides means for positioning said first component relative to said second component through uninterrupted one-handed contact with said releasing means, whereby said implement may be conveniently positioned relative to said associate unit.

14. In combination:
a first unit;
a second unit including at least one substantially straight appendage having an elastically deformable channel-like profile and lateral edges exposed in a generally common plane;
an implement-mount comprising means, including a planar member, for attaching said second unit to said first unit through constricting the appendage profile generally perpendicular with said common plane and thereby causing elastically influenced gripping between the appendage edges and said planar member.

15. The combination of claim 14, wherein said appendage comprises multiple resilient legs, each leg having at least one edge for gripping said implement-mount through torsional distortion around a longitudinal axis of said leg.

16. The combination of claim 15, wherein said legs are at least partially joined together through at least one flexible component, and said appendage includes operable means for flexing said flexible component to release the leg edges from said implement-mount.

17. The combination of claim 16, wherein said operable means additionally provides means for positioning said appendage relative to said implement-mount through uninterrupted one-handed contact with said operable means.

18. In combination:
a headgear;
an implement having a functional relationship with at least one human sense;
a mount for supporting said implement entirely from said headgear in said functional relationship and providing combined multidirectional positioning of said implement relative to said headgear, said mount including common means for commonly releasing, effecting said positioning, and re-engaging said implement from said mount through uninterrupted one-handed contact with said common means.

19. The combination of claim 18, wherein said implement includes at least one resilient appendage joined thereto, and said common means comprises means for resiliently deforming said appendage, whereby said appendage may be released from said mount.

20. The combination of claim 19, wherein said appendage includes a resilient channeled profile and said common means comprises means for deforming said profile.

21. The combination of claim 19, wherein said appendage has a substantially linear longitudinal axis and at least one exposed edge generally parallel to said axis; and said mount comprises means including a contact surface for torsioning said appendage around said axis to effect resiliently biased bearing of said edge on said surface.

22. The combination of claim 21, wherein said appendage includes members paired in torsional opposition.

23. In combination:
a headgear having at least one implement-mount joined thereto, said implement-mount including a constraint opening bounded by a bearing surface;
an implement including at least one semirigid appendage having exposed edges, an unconstrained resilient cross section dimensionally greater than said constraint opening, and means for manually deforming said cross section to dimensionally less than said constraint opening;
means for mounting said implement from said headgear wherein said constraint opening engages said appendage while constricting said cross section to create resiliently biased friction between said edges and said bearing surface, and said deforming means may be utilized to release said edges from frictional engagement with said bearing surface.

24. The combination of claim 23, wherein said appendage comprises paired members for providing resilient torsional opposition when said cross section is constricted.

25. The combination of claim 23, wherein said deforming means additionally provides means for positioning said implement relative to said headgear through uninterrupted one-handed contact with said deforming means.

26. A multipart device for use in holding one component relative to another component comprising:
a first part comprising two generally paired, side by side members, each member including a lengthwise periphery, a lengthwise axis and means for effecting turning resilience around said axis;
a second part for engaging said first part, said second part comprising a contact surface and means for turning each paired member around each axis oppositely of the other so as to effect resilient clutching of each of said periphery against said surface.

27. The device of claim 26, wherein said turning means causes said paired members to be disposed in substantially balanced resilient opposition.

28. The device of claim 26, wherein said contact surface includes a friction enhancing member, said periphery includes an edge, and said turning means causes said edge to clutch against the friction member.

29. The device of claim 26, wherein said paired members cooperate to define a resilient channel-like cross section having periphery exposed in a substantially common plane, and said turning means comprises means for distorting said cross section.

30. The device of claim 26, wherein said first and said second parts comprise means for providing combined pivotal and translational movement relative to one another.

31. The device of claim 26, further including means for declutching said first part from said second part while still engaged one to the other, thereby allowing repositioning of said first part relative to said second part.

* * * * *